(12) United States Patent
Seifert et al.

(10) Patent No.: US 8,644,932 B2
(45) Date of Patent: Feb. 4, 2014

(54) ASSESSING A LEAD BASED ON HIGH-FREQUENCY RESPONSE

(75) Inventors: Kevin R. Seifert, Forest Lake, MN (US); Christopher C. Stancer, Prescott, WI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/915,828

(22) Filed: Oct. 29, 2010

(65) Prior Publication Data
US 2012/0109246 A1    May 3, 2012

(51) Int. Cl.
*A61N 1/37*    (2006.01)
(52) U.S. Cl.
USPC .............................. 607/28; 607/27
(58) Field of Classification Search
USPC ....................................... 607/27, 28
See application file for complete search history.

(56) References Cited

U.S. PATENT DOCUMENTS

| | | | |
|---|---|---|---|
| 6,445,951 B1 * | 9/2002 | Mouchawar | 607/28 |
| 7,373,227 B2 | 5/2008 | Lu et al. | |
| 7,561,915 B1 | 7/2009 | Cooke et al. | |
| 2003/0144720 A1 | 7/2003 | Villaseca et al. | |
| 2007/0021814 A1 | 1/2007 | Inman et al. | |
| 2007/0083244 A1 | 4/2007 | Stevenson et al. | |
| 2007/0100407 A1 * | 5/2007 | Armstrong | 607/116 |
| 2007/0208383 A1 | 9/2007 | Williams | |
| 2007/0299490 A1 | 12/2007 | Yang et al. | |
| 2008/0262585 A1 | 10/2008 | Alexander et al. | |
| 2010/0106215 A1 * | 4/2010 | Stubbs et al. | 607/37 |
| 2011/0054554 A1 * | 3/2011 | Swerdlow | 607/5 |

FOREIGN PATENT DOCUMENTS

WO         98/42406 A1     10/1998

OTHER PUBLICATIONS

International Search Report and Written Opinion of PCT/US2011/034295, dated Nov. 3, 2011, 10 pp.
International Preliminary Report on Patentability from PCT/US2011/034295 dated May 10, 2013 (8 pages).

* cited by examiner

*Primary Examiner* — George Evanisko
(74) *Attorney, Agent, or Firm* — Michael J. Ostrom (57) ABSTRACT

In general, this disclosure is directed to techniques and circuitry to determine characteristics of an implantable lead associated with an implantable medical device (IMD). The implantable lead may be designed to be MRI-safe by having one or more components that attenuate frequencies associated with an MRI that, if left unreduced, may interfere with the performance of the lead and/or cause harm to the tissue in which the lead is implanted. The circuitry may transmit a signal through the lead and receive a response signal. The device may determine the lead characteristics by comparing the transmitted signal with the received signal. In addition to determining whether the lead is MRI-safe, the techniques of this disclosure may be also utilized to determine whether the lead is faulty.

40 Claims, 6 Drawing Sheets

ASSESSING A LEAD BASED ON HIGH-FREQUENCY RESPONSE

TECHNICAL FIELD

The invention relates to medical devices, and, more particularly, to detection of medical device states.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissues. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient. Other medical devices do not include leads, and instead include electrodes and/or sensors formed on or located within a housing of the device.

In systems that include medical leads, the leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry, such as signal generation and/or sensing circuitry. In some cases, the medical leads and the medical device housing are implantable within the patient. In systems that do not include medical leads, electrodes and/or sensors may be located within the medical device housing, which may be positioned at a location that allows delivery of therapeutic electrical signals or sensing of bioelectrical signals. Medical devices with a housing configured for implantation within the patient may be referred to as implantable medical devices.

SUMMARY

In general, the disclosure describes techniques for determining a characteristic of an implantable medical lead based on a response of the lead to application of a relatively high frequency signal. For example, based on the response, an implantable medical device (IMD) or other device may determine whether a lead coupled to the IMD is designed to be MRI-safe or safe for other imaging modalities, e.g., the lead includes electromagnetic field mitigation circuitry. As another example, based on the response, an IMD or other device may determine whether the electromagnetic field mitigation circuitry is operating properly as to dissipate MRI energy that may damage the lead and/or cause damage in the tissue where the lead is implanted, e.g., whether an MRI-safe lead attached to the IMD is in fact MRI-safe.

A signal generator within the IMD may generate a relatively high frequency signal, and apply the signal to the lead. The frequency of the signal may be on the order of approximately 1 MHz or greater (e.g., approximately 64 MHz). The IMD may additionally include circuitry to measure a response of the lead to the signal. Based on the response, the lead characteristic, e.g., whether the lead includes properly operating electromagnetic field mitigation circuitry, may be determined. Additionally or alternatively, the response of the lead may indicate whether a lead related condition or lead fault, e.g., a fracture, is present in the lead. The measured response of the lead to the relatively high frequency signal may include, for example, impedance during application of the signal, or a characteristic of a reflected signal during application of the relatively high-frequency signal.

In one example, the disclosure is directed to a method comprising transmitting, by a device, a signal through at least one medical lead implanted within at least one anatomical region of a patient, wherein the at least one medical lead is coupled to an electrical component configured to attenuate a frequency of energy, receiving, by the device, a response signal, analyzing the response signal, and determining characteristics of the at least one medical lead based on the analysis, wherein the characteristics include at least one of an indication whether the electrical component attenuates the frequency or a detected fault in the at least one medical lead.

In another example, the disclosure is directed to a medical system comprising a signal generator that transmits a signal through at least one medical lead implanted within at least one anatomical region of a patient, wherein the at least one medical lead is coupled to an electrical component configured to attenuate a frequency of energy, a sensing module that receives a response signal, an analysis module that analyzes the response signal, and at least one processor that determines characteristics of the at least one medical lead based on the analysis, wherein the characteristics include at least one of an indication whether the electrical component attenuates the frequency or a detected fault in the at least one medical lead.

In another example, the disclosure is directed to a medical system comprising means for transmitting, by a device, a signal through at least one medical lead implanted within at least one anatomical region of a patient, wherein the at least one medical lead is coupled to an electrical component configured to attenuate a frequency of energy, means for receiving, by the device, a response signal, means for analyzing the response signal, and means for determining characteristics of the at least one medical lead based on the analysis, wherein the characteristics include at least one of an indication whether the electrical component attenuates the frequency or a detected fault in the at least one medical lead.

In another example, the disclosure is directed to an article of manufacture comprising a computer-readable medium comprising instructions that, upon execution, cause a processor to transmit, by a device, a signal through at least one medical lead implanted within at least one anatomical region of a patient, wherein the at least one medical lead is coupled to an electrical component configured to attenuate a frequency of energy, receive, by the device, a response signal, analyze the response signal, and determine characteristics of the at least one medical lead based on the analysis, wherein the characteristics include at least one of an indication whether the electrical component attenuates the frequency or a detected fault in the at least one medical lead.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein.

The details of one or more examples are set forth in the accompanying drawings and the description below. Other features, objects, and advantages will be apparent from the description and drawings, and from the claims.

DETAILED DESCRIPTION

This disclosure describes various techniques for verifying characteristics of components of an IMD, including determining whether an implantable medical lead is MRI-safe and whether the lead is functional. Implantable medical leads typically include a lead body containing one or more elongated electrical conductors that extend through the lead body from a connector assembly provided at a proximal lead end to one or more electrodes located at the distal lead end or elsewhere along the length of the lead body. The conductors connect signal generation and/or sensing circuitry within an associated implantable medical device housing to respective electrodes or sensors. Some electrodes may be used for both delivery of therapeutic signals and sensing. Each electrical conductor is typically electrically isolated from other electrical conductors and is encased within an outer sheath that electrically insulates the lead conductors from body tissue and fluids.

Medical lead bodies implanted for cardiac applications tend to be continuously flexed by the beating of the heart. Other stresses may be applied to the lead body, including the conductors therein, during implantation or lead repositioning. Patient movement can cause the route traversed by the lead body to be constricted or otherwise altered, causing stresses on the lead body and conductors. In rare instances, such stresses may fracture a conductor within the lead body. The fracture may be continuously present, or may intermittently manifest as the lead flexes and moves.

Additionally, the electrical connection between medical device connector elements and the lead connector elements can be intermittently or continuously disrupted. For example, connection mechanisms, such as set screws, may be insufficiently tightened at the time of implantation, followed by a gradual loosening of the connection. Also, lead pins may not be completely inserted.

Lead fracture, disrupted connections, or other causes of short circuits or open circuits may be referred to, in general, as lead related conditions or lead faults. In the case of cardiac leads, sensing of an intrinsic heart rhythm through a lead can be altered by lead-related conditions. Identifying lead-related conditions may be challenging, particularly in a clinic, hospital, or operating room setting, due to the often intermittent nature of lead-related conditions. Identification of lead-related conditions may allow modifications of the therapy or sensing, or lead replacement.

Once implanted, an IMD generally remains within the patient for a significant duration of time, and can be exposed to various environmental factors. For example, the patient may undergo a magnetic resonance imaging (MRI) procedure or other high frequency imaging procedures. It is generally desirable to avoid or mitigate certain effects of MRI or other imaging modalities on an IMD, or a patient in which an IMD is implanted.

For example, electromagnetic fields, such as those emitted during an MRI or other imaging procedure may induce currents or energy in the conductors of a lead coupled to an IMD. The sensing circuitry within an IMD may be sensitive to the currents or energy induced in the conductors. Moreover, the currents or energy could lead to heating of the lead, which could in turn cause tissue necrosis of the patient in which the lead is implanted.

For these reasons, it has been proposed to include components that alter the characteristics of leads or IMDs (e.g., high-frequency electromagnetic field mitigation circuitry within leads or IMDs) to make such leads or IMDs "MRI-safe." Generally, such circuitry is designed to dissipate energy or current on the lead at or above a certain frequency, e.g., radio frequency (RF) energy. Furthermore, it has been proposed to place the operational circuitry of the IMD in an MRI or imaging mode, which generally reduces the functionality of the IMD to avoid any undesired behavior that may occur due to electromagnetic interference emitted by the MRI or other imaging system.

As implantable device and lead technology improves, the devices and leads become more sophisticated and capable of tolerating many conditions and activities in the surrounding environment. One such example is MRI-safe leads, designed to dissipate MRI RF energy (e.g., 64 MHz RF energy for a 1.5 T MRI scanner) that, if left unreduced, can cause lead tip heating. Lead tip heating may result in increased pacing capture threshold and/or heart tissue necrosis.

Therefore, prior to an MRI or other imaging procedure, it may be desirable to safely confirm that an implanted device and/or leads are MRI-safe and that the RF mitigation circuitry is functioning properly. Using the techniques of this disclosure, e.g., prior to a procedure that requires using an MRI machine, or other source of electromagnetic energy or interference, pulses with a specific, relatively high frequency may be applied to the lead. A response of the lead to the applied signal, such as an impedance or a reflected signal, may then be determined. Based on the response, a determination is made regarding a characteristic of the lead, e.g., whether the lead is MRI-safe. In addition to the MRI-safe determination, another characteristic of the lead that may be determined based on the response may be whether any faults are present in the lead, or in its contact with patient tissue or connection to the IMD. In this manner, the same techniques may be used to detect whether an implantable electric lead is not faulty and confirm that the lead is also MRI-safe.

Figure 1:
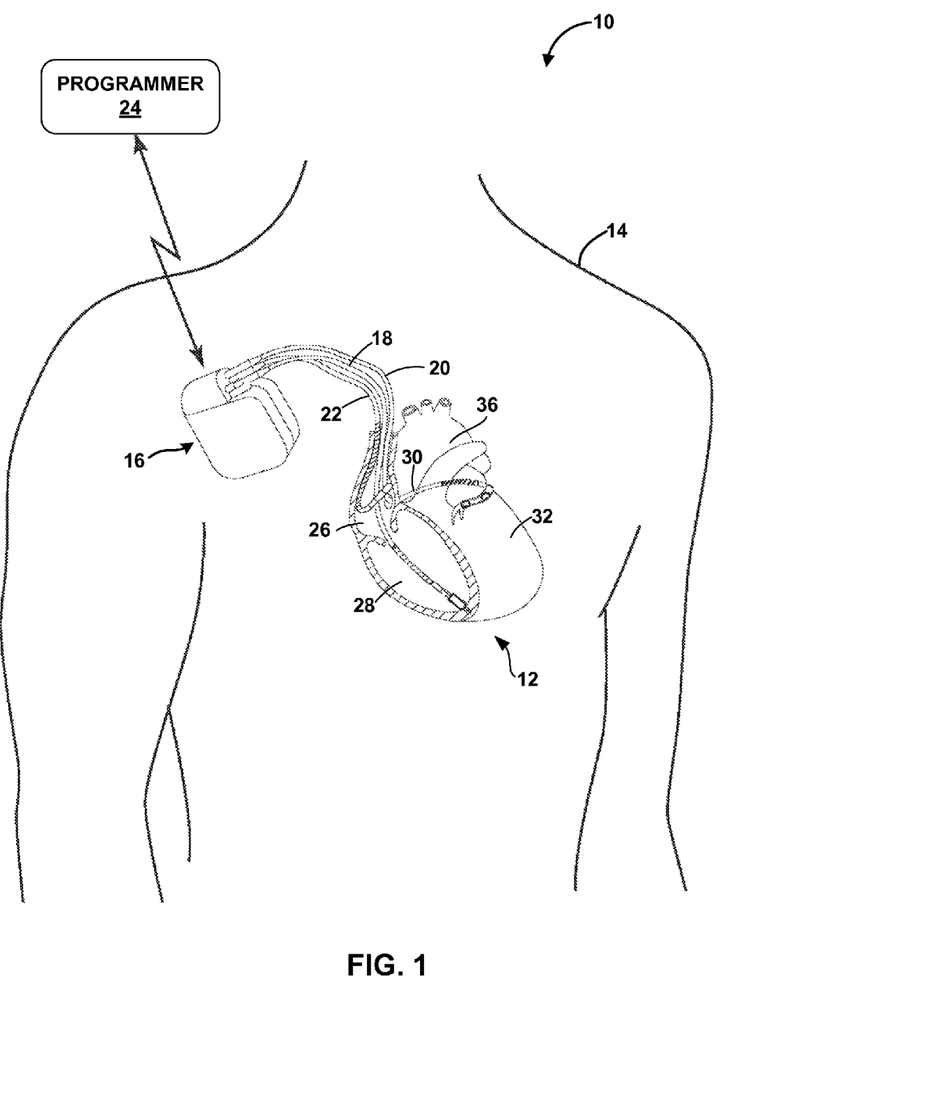
FIG. 1 is a conceptual diagram illustrating an implantable medical device.

FIG. 1 is a conceptual diagram of an implantable medical device. More particularly, FIG. 1 is a conceptual diagram illustrating an example system 10 that may be used to monitor and/or provide therapy to heart 12 of patient 14. Patient 14 ordinarily, but not necessarily, will be a human.

System 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. In accordance with certain techniques of this disclosure, IMD 16 may include circuitry to detect and confirm whether one or more leads 18, 20, and 22 are operating as expected, as will be described in more detail below. For example, IMD 16 may transmit one or more signals through one of leads 18, 20, and 22, and measure impedance or a reflected signal during transmittal of the signal through one or more leads 18, 20, and 22. IMD 16 may then analyze the impedance or reflected signal to determine a characteristic of the lead through which IMD 16 transmitted the signal. Based on the analysis, IMD 16 may determine whether the lead is operating as expected.

In some examples, leads 18, 20, and 22 may be modified to operate in environments that may be otherwise detrimental to the operation of IMD 16 and/or leads 18, 20 and 22, e.g., in the presence of MRI or other electromagnetic fields. For example, one or more of leads 18, 20 and 22 may include electromagnetic field mitigation circuitry. IMD 16 may apply the relatively high-frequency signal to one or more of the leads in order to determine whether the lead 18, 20 or 22 includes electromagnetic field mitigation circuitry and/or whether the electromagnetic field mitigation circuitry is operating properly to mitigate the effect(s) of electromagnetic fields on the lead. Thus, in some examples, IMD 16 may transmit a signal with a particular frequency (e.g., a relatively high frequency) to confirm whether a lead designed to be MRI-safe is operating accordingly.

Additionally, IMD 16 may utilize the results of the same analysis to detect any lead faults, e.g., lead fractures. In one example, IMD 16 may periodically apply a signal, to a lead, e.g., automatically or in response to a user command, for testing lead operability. IMD 16 may test whether a lead includes properly-operating electromagnetic field mitigation circuitry in response to a user command, e.g., a command for the IMD to enter a MRI-safe mode of operation. In some examples, IMD 16 may alert a user (e.g., a clinician via a programmer 24 or a computing network) if a fault is detected in lead operation.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. Leads 18, 20, and 22 may include electrical components designed to reduce the effects of electromagnetic fields on leads 18, 20 and 22 or IMD 16, e.g., electromagnetic field mitigation circuitry (not shown in FIG. 1). Some examples of electromagnetic field mitigation circuitry that can reduce or dissipate the effects of electromagnetic fields, e.g., MRI RF fields, include inductive chokes, capacitive shunts, traps, shields, and higher inductance lead bodies. In general, such electromagnetic field mitigation circuitry works to prevent current at certain, relatively high, frequencies, e.g., RF or other frequencies associated with MRI or other imaging procedures, on the conductors within the leads.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, and 22, or a power source of IMD 16. The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies.

In one example in accordance with techniques of this disclosure, the user may use programmer 24 to verify operability of leads 18, 20, and 22 generally or in certain environments. For example, the user may use programmer 24 to control IMD 16 to apply a signal of a particular frequency to one or more of leads 18, 20, and 22 and determine, based on a response of the leads during application of the signal, whether leads 18, 20, and 22 are operating in an expected manner, e.g., are fault-free and/or MRI safe. The user may also use programmer 24 to receive visual indications of the functionality of IMD 16 and the leads.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
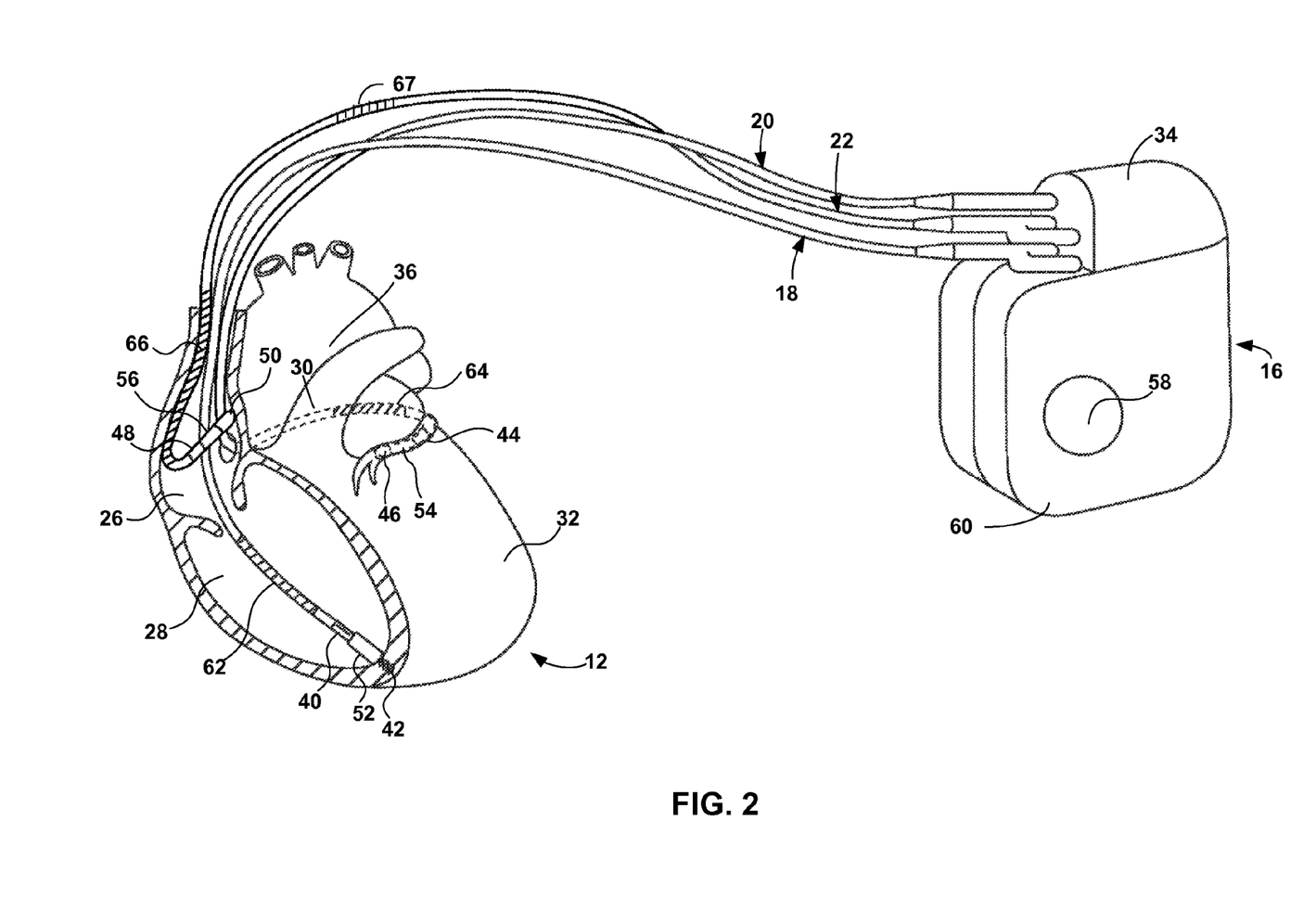
FIG. 2 is a conceptual diagram further illustrating the IMD of FIG. 1 in conjunction with the heart.

FIG. 2 is a conceptual diagram further illustrating the IMD of FIG. 1 in conjunction with the heart. Leads 18, 20, 22 may be electrically coupled to a signal generator and a sensing module of IMD 16 via connector block 34.

Each of the leads 18, 20, 22 includes an elongated insulative lead body carrying one or more conductors. Bipolar electrodes 40 and 42 are located adjacent to a distal end of lead 18. In addition, bipolar electrodes 44 and 46 are located adjacent to a distal end of lead 20 and bipolar electrodes 48 and 50 are located adjacent to a distal end of lead 22. Electrodes 40, 44 and 48 may take the form of ring electrodes, and electrodes 42, 46 and 50 may take the form of extendable helix tip electrodes mounted retractably within insulative electrode heads 52, 54 and 56, respectively.

Leads 18, 20, 22 also include elongated intracardiac electrodes 62, 64 and 66 respectively, which may take the form of a coil. In addition, one of leads 18, 20, 22, e.g., lead 22 as seen in FIG. 2, may include a superior vena cava (SVC) coil 67 for delivery of electrical stimulation, e.g., transvenous defibrillation. For example, lead 22 may be inserted through the superior vena cava and SVC coil 67 may be placed, for example, at the right atrial/SVC junction (low SVC) or in the left subclavian vein (high SVC). Each of the electrodes 40, 42, 44, 46, 48, 50, 62, 64, 66 and 67 may be electrically coupled to a respective one of the conductors within the lead body of its associated lead 18, 20, 22, and thereby individually coupled to the signal generator and sensing module of IMD 16. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60.

IMD 16 may sense electrical signals attendant to the depolarization and repolarization of heart 12 via electrodes 40, 42, 44, 46, 48, 50, 58, 62, 64, 66 and 67. The electrical signals are conducted to IMD 16 via the respective leads 18, 20, 22, or in the case of housing electrode 58, a conductor coupled to the housing electrode. IMD 16 may sense such electrical signals via any bipolar combination of electrodes 40, 42, 44, 46, 48, 50, 58, 62, 64, 66 and 67. Furthermore, any of the electrodes 40, 42, 44, 46, 48, 50, 58, 62, 64, 66 and 67 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. For example, electrodes 40, 42, and/or 58 may be used to deliver RV pacing to heart 12. Additionally or alternatively, electrodes 44, 46, and/or 58 may be used to deliver LV pacing to heart 12, and electrodes 48, 50 and/or 58 may be used to deliver RA pacing to heart 12.

Furthermore, IMD 16 may deliver defibrillation pulses to heart 12 via any combination of elongated electrodes 62, 64, 66 and 67, and housing electrode 58. Electrodes 58, 62, 64, 66 may also be used to deliver cardioversion pulses to heart 12. Electrodes 62, 64, 66 and 67 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIGS. 1 and 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. Other examples of therapy systems may include a single lead that extends from IMD 16 into right atrium 26 or right ventricle 28, or two leads that extend into a respective one of the right ventricle 28 and right atrium 26 (not shown). The example of FIGS. 1 and 2 includes a single electrode per chamber of heart 12 engaged with the wall of heart 12, e.g., free wall, for that chamber. Other examples may include multiple electrodes per chamber, at a variety of different locations on the wall of heart. The multiple electrodes may be carried by one lead or multiple leads per chamber.

In accordance with certain aspects of this disclosure, IMD 16 may include circuitry for monitoring specific functionality and operability of different components such as, for example, leads associated with IMD 16. For example, IMD 16 and leads may be designed for compatibility with different environments, such that operability of IMD 16 and the leads and safety to the patient are maintained. In one example, IMD 16 and leads 18, 20, and 22 may be compatible with MRI energies, such that, when in an MRI environment, the leads and/or IMD 16 continue functioning properly and safely. The modifications to the leads to ensure MRI-safety, e.g., inclusion of magnetic field mitigation circuitry, may change the electrical characteristics of the leads relative to standard leads (non MRI-safe). The monitoring circuitry in IMD 16 may utilize knowledge of these characteristics to determine whether the MRI-safe leads are functioning properly. In one example, IMD 16 may transmit signals through one or more of the leads and analyze a received response signal to determine the characteristics of the lead, and verify that the leads are still MRI-safe. In one example, IMD 16 may periodically monitor the lead functionality. In another example, IMD 16 may perform testing of the leads during preparation time for an MRI scan.

The disclosure generally refers to IMD 16 as performing monitoring of the leads and initiating testing, but the disclosure is not so limited. In other examples, a user may initiate testing of the leads using programmer 24. In response, IMD 16 may perform the testing to confirm operability of the leads and send a signal to programmer 24 indicating the results of the testing. Additionally, while the techniques of this disclosure are discussed in terms of MRI-related activities, it should be understood that these techniques may be modified to test for other types of activities that may affect the operation of implantable devices.

Figure 3A:
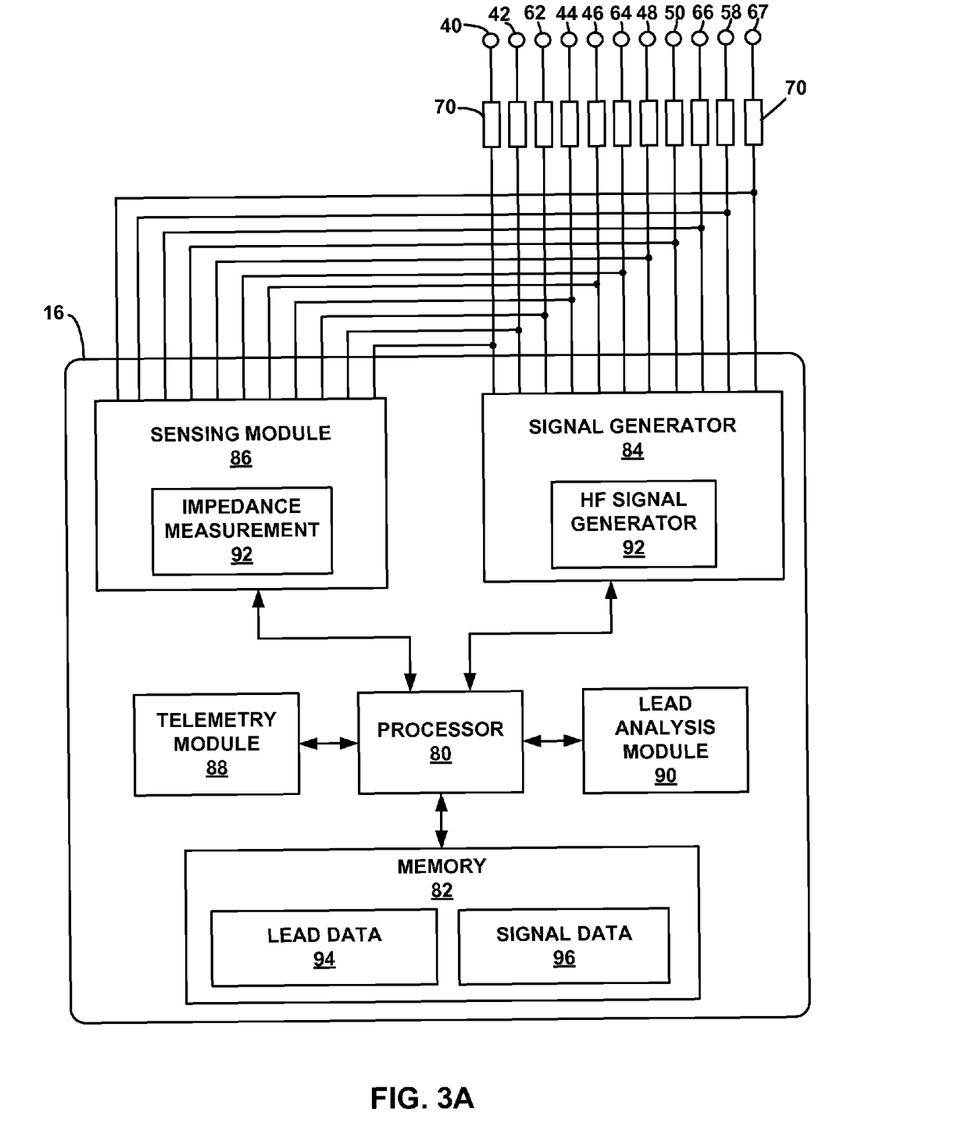
FIG. 3A is a functional block diagram illustrating an example configuration of an IMD that may be used to implement certain techniques of this disclosure.

FIG. 3A is a functional block diagram illustrating an example configuration of IMD 16 that may be used to implement certain techniques of this disclosure. In the illustrated example, IMD 16 includes a processor 80, memory 82, signal generator 84, sensing module 86, telemetry module 88, and lead analysis module 90. As FIG. 3A illustrates, signal generator 84 may include a high frequency (HF) signal generator 92. HF signal generator 92 may generate signals with frequencies that may be similar to electromagnetic fields generated during imaging, e.g., RF or other frequencies associated with MRI or other imaging procedures. HF signal generator 92 may generate relatively high frequencies that IMD 16 may utilize to monitor operation of different IMD components, e.g., leads or electrodes. IMD 16 may transmit signals generated by HF signal generator 92 and measure a response, which may include receiving a response signal via sensing module 86. Lead analysis module 90 analyzes the received response signal data to determine characteristics of the leads on which IMD 16 transmitted the signals. Lead analysis module 90 may be implemented as software, firmware, hardware or any combination thereof. In some example implementations, lead analysis module 90 may be a software process implemented in or executed by processor 80. Memory 82 is one example of a non-transitory, computer-readable storage medium that includes computer-readable instructions that, when executed by processor 80, cause IMD 16 and processor 80 to perform various functions attributed to IMD 16 and processor 80 in this disclosure. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

As indicated above, the techniques described in this disclosure may be implemented by IMD 16 to determine whether the operation of the leads is consistent with their design. Specifically, the leads associated with IMD 16 may be designed to withstand conditions in environments that present factors, which when left unaccounted for, may cause harm to the IMD, leads, and/or the patient. In one example, the leads may be designed to function safely in environments that may be otherwise harmful to IMD 16 and/or to tissue or organs receiving therapy from IMD 16. For example, the leads may include mitigation circuitry 70 that ensures tolerance and continued operability in environments such as, for example, an MRI environment, which introduce energy levels that can cause overheating of lead tips, resulting in damage to tissue in which the leads are implanted or to which the leads supply therapy. Components 70 may be, for example, electromagnetic field mitigation circuitry, which may include, for example, inductive chokes, capacitive shunts, traps, shields, and higher inductance lead bodies. HF signal generator 92 may generate signals at a relatively high frequency that is suppressed or otherwise mitigated by mitigation circuitry 70.

Periodically or prior to entering an MRI environment, IMD 16 may utilize HF signal generator 92 to generate and transmit signals at relatively high frequency over one or more leads or electrodes, and may utilize one or more leads or electrodes to sense a response signal. Data associated with the transmitted and received signals may be stored in a signal data memory 96. Lead data 94 may include data associated with the leads indicating expected lead characteristics according to the lead design, e.g., signal characteristics for a lead designed to be MRI-safe, lead length, and the like. Lead analysis module 90 may utilize the signal data and lead data to determine the characteristics of the lead and whether the leads are operating as expected.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 in this disclosure may be embodied as software, firmware, hardware or any combination thereof.

In some examples, processor 80 controls signal generator 84 to deliver stimulation therapy to heart 12 according to a selected one or more of therapy programs, which may be stored in memory 82. For example, processor 80 may control signal generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, 66, and 67 e.g., via conductors of the respective leads 18, 20, 22, or, in the case of housing electrode 58, via an electrical conductor disposed within housing 60 of IMD 16. In some examples, signal generator 84 is configured to generate and deliver electrical stimulation therapy to heart 12. For example, signal generator 84 may deliver defibrillation shocks as therapy to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module, and processor 80 may use the switch module to select which of the available electrodes are used to deliver such stimulation. The switch module may include a switch array, switch matrix, multiplexer, or any other type of switching device suitable to selectively couple stimulation energy to selected electrodes.

As discussed above, signal generator 84 may include HF signal generator 92, which is capable of generating signals at relatively high frequencies intended for testing and monitoring purposes, in accordance with techniques of this disclosure. In one example, a high frequency signal may be generated to test whether leads 18, 20, and 22 or electrodes associated with IMD 16 are configured for operation in certain environments (e.g., MRI scan environment) that may be otherwise harmful to the device, leads or electrodes, and/or patient. Processor 80 may use the switch module in signal generator 84 to select leads for testing by selecting the appropriate electrodes and transmitting generated HF signals on the selected electrodes.

In some examples, sensing module 86 monitors signals from at least one of electrodes 40, 42, 44, 46, 48, 50, 58, 62, 64, 66 or 67 in order to monitor electrical activity of heart 12. Sensing module 86 may also include a switch module. In some examples, processor 80 may select the electrodes that function as sense electrodes via the switch module within sensing module 86.

Sensing module 86 may include one or more detection channels (not shown), each of which may comprise an amplifier. The detection channels may be used to sense the cardiac signals. Some detection channels may detect cardiac events, such as R- or P-waves, and provide indications of the occurrences of such events to processor 80. One or more other detection channels may provide the signals to an analog-to-digital converter, for processing or analysis by processor 80. In some examples, processor 80 may store the digitized versions of signals from one or more selected detection channels in memory 82 as EGM signals. In response to the signals from processor 80, the switch module within sensing module 86 may couple selected electrodes to selected detection channels, e.g., for detecting events or acquiring an EGM in a particular chamber of heart 12.

In one example, signals received in response to transmitted HF signals for testing or monitoring purposes may be processed by processor 80. Processor 80 may utilize lead analysis module 90 to determine lead characteristics based on the received response signal, relative to the transmitted HF signal. In one example, based on the analysis, processor 80 may determine whether the tested lead is operating in accordance with its design, e.g., MRI-safe. Additionally, processor 80 may detect faults in the tested lead based on the analysis of the received response signal. In this manner, processor 80 may determine based on the same analysis results whether there is a fault in a tested lead (e.g., breakage, shifting, or other flaws that may alter electrical properties of leads) and/or whether the lead is behaving in a manner consistent with its design (e.g., MRI-safe). In some examples, processor 80 may determine based on the analysis results whether a lead is MRI-safe without having prior knowledge whether the lead is designed to be MRI-safe.

As FIG. 3A illustrates, in addition to program instructions, memory 82 may store lead data 94 and signal data 96. Lead data 94 may be data associated with leads 18, 20, and 22 such as, for example, electrical characteristics of the leads resulting from altering their design (e.g., by adding mitigation circuitry 70) to make them effectively and safely operable in conditions that may otherwise have adverse effects on the operation of the leads and/or the patient. In some examples, an IMD may be modified to reduce harmful effects in an environment such as, for example, during an MRI scan, where leads can become harmful from MRI RF energy. For example, the MRI RF energy can cause heating of the tip of the leads, resulting in damage to surrounding tissue. As another example, the MRI signals may affect the operation of the leads and/or the IMD resulting in delivery of unnecessary stimulation, which can damage the target organ (e.g., heart). Therefore, electrical components 70 (electromagnetic field mitigation circuitry, e.g., chokes, shunts, traps, and the like) may be added to leads to dissipate and reduce harmful effects of MRI RF energy. The added components may change electrical properties of the associated leads, and the characteristics of the modified leads may be known (e.g., expected impedance, effect on frequency and amplitude of a waveform, and the like). The expected characteristics may be stored as lead data 94 in memory 82.

Signal data 96 may include transmitted signal and received response signal data. When processor 80 causes the generation and transmission of a high frequency signal from HF signal generator 92, processor 80 may store properties of the transmitted signal (e.g., frequency, wavelength, amplitude, and the like) in signal data 96. Subsequently, when processor 80 receives a response signal via sensing module 86, processor 80 may store properties of the received signal in signal data 96. Processor 80 may also store additional data related to the received signal, e.g., timing information. Processor 80 may then utilize lead analysis module 90 to analyze signal data 96, including transmitted signal data and received signal data and characterize the lead(s) used to transmit the signal.

Processor 80 may determine based on the analysis and lead data 94 whether the lead(s) is operating properly. The analysis may allow processor 80 to detect faults with the lead(s), and verify the lead's ability to operate without causing harm or damage to the IMD and/or patient. In some examples, IMD 16 may perform this testing periodically or during a preparation period prior to an MRI scan. In some examples, processor 80 may provide an indication regarding the operation of the lead(s). For example, processor 80 may communicate the indication to a remote associated device (e.g., a programmer) via telemetry module 88. In one example, a user (e.g., clinician) may receive an indication on the programmer associated with IMD 16 (e.g., programmer 24 of FIG. 1) indicating that the leads are operating properly and that it would be safe to perform an MRI scan. In another example, the user may receive an indication on the programmer that there are problems with the leads and that an MRI scan may be harmful to the IMD and/or patient. In this example, processor 80 may indicate whether the problem with the lead indicates detection that the lead is not operating as expected (e.g., not MRI-safe) or if the lead is faulty (e.g., breakage or shifting of the lead, or other flaws that may alter electrical properties of leads).

Figure 3B:
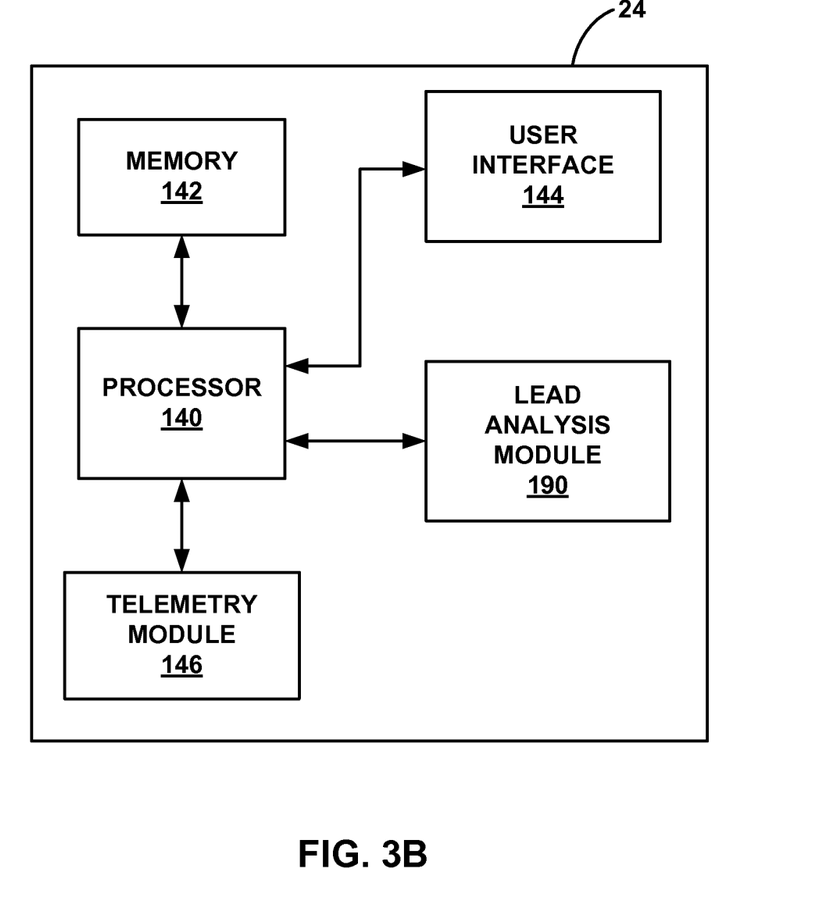
FIG. 3B is a functional block diagram illustrating an example configuration of an external programmer that facilitates user communication with an IMD.

FIG. 3B is a functional block diagram illustrating an example configuration of an external programmer that facilitates user communication with an IMD. As shown in FIG. 3B, programmer 24 may include a processor 140, memory 142, user interface 144, telemetry module 146, power source 148, and lead analysis module 190. Programmer 24 may be a dedicated hardware device with dedicated software for programming of IMDs 16. Alternatively, programmer 24 may be an off-the-shelf computing device running an application that enables programmer 24 to program IMDs 16.

A user may use programmer 24 to select therapy programs (e.g., sets of stimulation parameters), generate new therapy programs, modify therapy programs through individual or global adjustments or transmit the new programs to a medical device, such as IMDs 16. The clinician may interact with programmer 24 via user interface 144, which may include display to present graphical user interface to a user, and a keypad or another mechanism for receiving input from a user. In addition, the user may receive data from IMDs 16 indicating operating conditions of IMD 16 and/or leads connected to IMD 16 via programmer 24.

Processor 140 can take the form of one or more microprocessors, DSPs, ASICs, FPGAs, programmable logic circuitry, or the like, and the functions attributed to processor 140 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMDs 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12. Telemetry module 146 may be similar to telemetry module 88 of IMD 16 (FIG. 3A).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 of programmer 24 and/or one or more processors of one or more networked computers may perform all or a portion of the techniques described herein with respect to processor 80 and IMD 16. For example, processor 140 or another processor may receive lead data and signal data from IMD 16, and utilize lead analysis module 190 to determine lead characteristics to determine whether a test lead of IMD 16 is operating correctly, e.g., MRI-safe and/or presence of lead faults, as described above. Processor 140 may utilize user interface 144 to display to a user results of the lead analysis. In one example, lead analysis may be performed in IMD 16, and results of the analysis may be communicated to programmer 24, which may display the results to the user.

Figure 4:
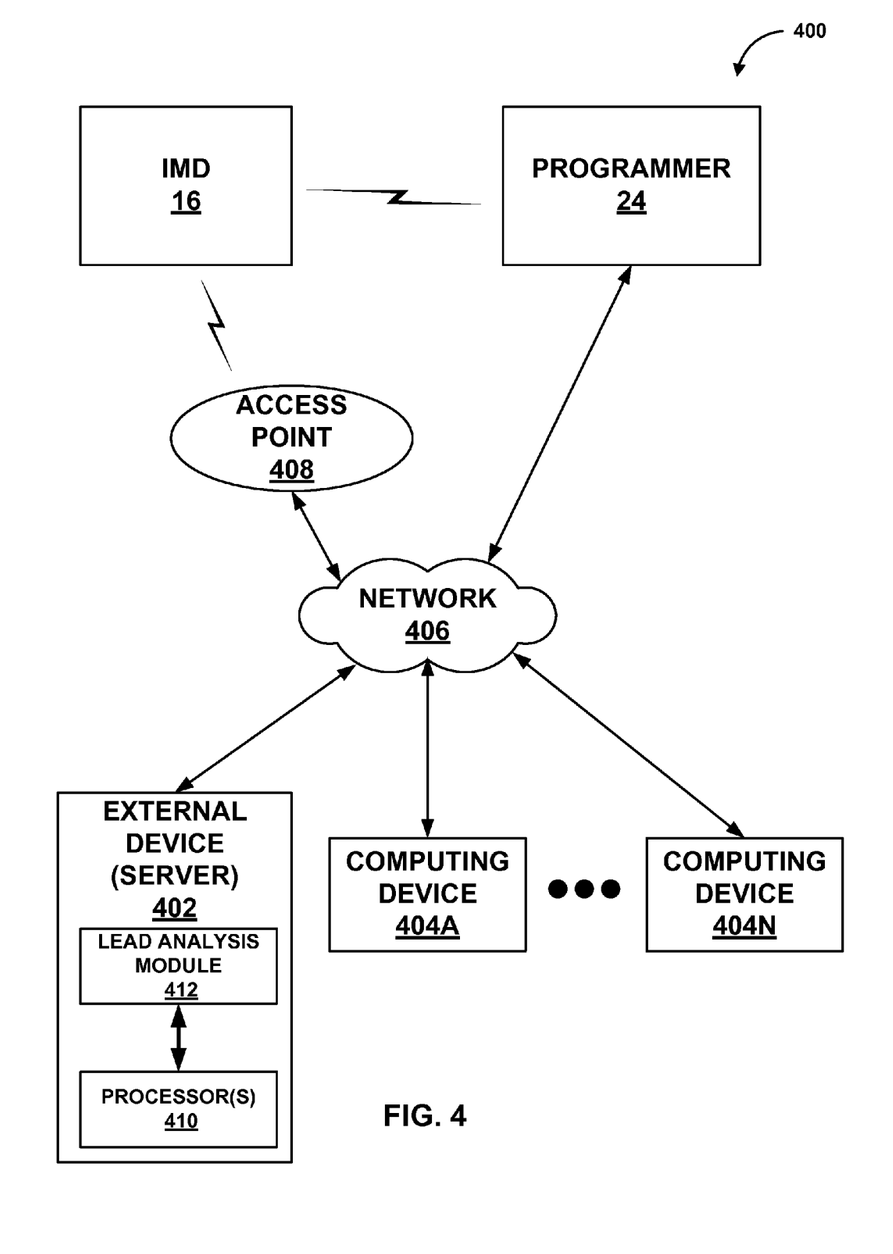
FIG. 4 is a block diagram illustrating an example system that includes an external device and one or more computing devices coupled to the IMD and programmer of FIG. 1 via a network.

FIG. 4 is a block diagram illustrating an example system 400 that includes an external device, such as a server 402, and one or more computing devices 404A-404N, that are coupled to the IMD 16 and programmer 24 of FIG. 1 via a network 406. In this example, IMD 16 may use its telemetry module 88 to communicate with programmer 24 via a first wireless connection, and to communication with an access point 608 via a second wireless connection. In the example of FIG. 4, access point 408, programmer 24, server 402, and computing devices 404A-404N are interconnected, and able to communicate with each other, through network 406. In some cases, one or more of access point 408, programmer 24, server 402, and computing devices 404A-404N may be coupled to network 406 through one or more wireless connections. IMD 16, programmer 24, server 402, and computing devices 404A-404N may each comprise one or more processors, such as one or more microprocessors, DSPs, ASICs, FPGAs, programmable logic circuitry, or the like, that may perform various functions and operations, such as those described herein.

Access point 408 may comprise a device that connects to network 406 via any of a variety of connections, such as telephone dial-up, digital subscriber line (DSL), or cable modem connections. In other examples, access point 408 may be coupled to network 406 through different forms of connections, including wired or wireless connections. In some examples, access point 408 may be co-located with patient 14 and may comprise one or more programming units and/or computing devices (e.g., one or more monitoring units) that may perform various functions and operations described herein. For example, access point 408 may include a home-monitoring unit that is co-located with patient 14 and that may monitor the activity of IMD 16.

In some cases, server 402 may be configured to provide a secure storage site for data that has been collected from IMD 16 and/or programmer 24. Network 406 may comprise a local area network, wide area network, or global network, such as the Internet. In some cases, programmer 24 or server 402 may assemble data in web pages or other documents for viewing by trained professionals, such as clinicians, via viewing terminals associated with computing devices 404A-404N. The illustrated system of FIG. 4 may be implemented, in some aspects, with general network technology and functionality similar to that provided by the Medtronic CareLink® Network developed by Medtronic, Inc., of Minneapolis, Minn.

In some examples, processor 410 of server 402 may be configured to receive signal and lead information from IMD 16 for processing by lead analysis module 412 in the manner described throughout this disclosure. In other examples, processor 410 may receive data processed by a lead analysis module, e.g., data processed by lead analysis module 90 of IMD 16. Lead analysis module 412 may determine characteristics of leads associated with IMD 16 and determine whether the leads are operating as designed (e.g., MRI-safe) and detect faults with the leads using any of the techniques described in this disclosure. Processor 410 may provide alerts to users, e.g., to the patient via access point 408 or to a clinician via one of computing devices 404, identifying conditions, e.g., leads are or are not MRI-safe, or leads have faults like breakage. Processor 410 may suggest to a clinician, e.g., via programmer 24 or a computing device 404, a solution to a faulty lead or a lead that is not MRI-safe, such as replacing the identified lead, or not proceeding with a scheduled imaging operation or other procedure. Processor 410 may also adjust or control the delivery of therapy by IMD 16, e.g., electrical stimulation therapy and/or a therapeutic substance, via network 406.

Figure 5:
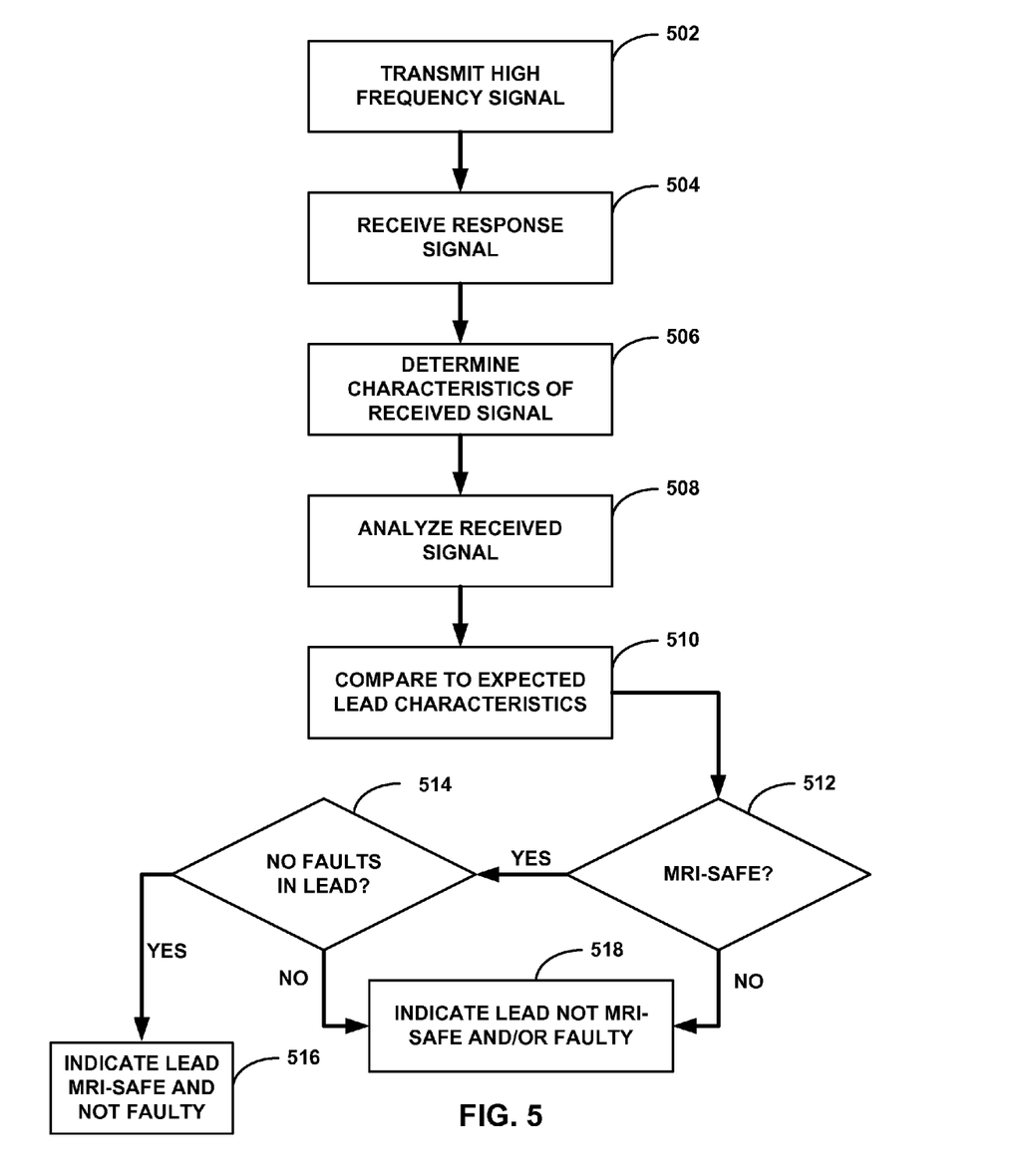
FIG. 5 is a flow diagram of an example method of determining characteristics of a lead in accordance with this disclosure.

FIG. 5 is a flow diagram of an example method of determining characteristics of a lead in accordance with this disclosure. As noted above, lead analysis module 90 of IMD 16 (FIG. 3) or lead analysis module 412 of external device 402 (FIG. 4) may be used to perform some or all of the calculations and decisions in order to detect the condition or characteristics of an implantable electrical element (e.g., lead).

Implantable electrical elements such as, for example, leads associated with IMDs may be affected by their surrounding environment (e.g., imaging devices and other sources of electromagnetic fields). In some situations, the effect of the surrounding environment may be minimal and may not change the characteristics of a lead or the leads operability. However, in some environments, such as within or proximate to MRI scanners, a lead's characteristics and operation may be greatly altered, and if not detected and/or changed, the consequences may be detrimental (e.g., cause damage to lead, IMD, and/or patient). Therefore, it may be important to ensure that implantable devices and leads are protected against harm that can be caused by different environments, e.g., MRI scanners. While the techniques of this disclosure are discussed in terms of MRI scanners, it should be understood that these techniques may be modified for or applied to determining the operability of leads in other environments that may present harmful conditions to the device and/or patient, such as other imaging devices and other sources of electromagnetic fields, e.g., electrosurgical equipment, such as electrocautery or ablation equipment.

As discussed above, leads coupled to IMDs may be made MRI-safe by including electrical components (e.g., electromagnetic field mitigation circuitry) that reduce or dissipate MRI RF energy (e.g., 64 MHz range for a 1.5 T MRI scanner). Some example electrical components that can be added to the leads may be inductive chokes, capacitive shunts, traps, shields, and higher inductance lead bodies, and the like. Adding such components changes the electrical characteristics (e.g., impedance) of the leads at different frequencies, and with proper tuning, specific harmful high frequencies, such as those associated with MRI scanner, may be attenuated. In some examples, the components may be added at any location on the lead and used to determine MRI-safety conditions. In other examples, components may be added at the distal end of a lead, which changes the characteristics of the distal end of the lead, and which may be beneficial in detecting whether the lead is MRI-safe and to detect lead faults (e.g., breakage). In other examples, components may be added to the tip of the lead. Examples of some of the electrical components listed above are described in U.S. patent application Ser. No. 11/555,111 filed on Oct. 31, 2006 and entitled "RADIOFREQUENCY (RF)-SHUNTED SLEEVE HEAD AND USE IN ELECTRICAL STIMULATION LEADS," U.S. patent application Ser. No. 11/741,568 filed on Apr. 27, 2007 and is entitled "MEDICAL ELECTRICAL LEAD BODY DESIGNS INCORPORATING ENERGY DISSIPATING SHUNT," and U.S. patent application Ser. No. 10/059,598 filed on Jan. 29, 2002 and is entitled "ELECTROMAGNETIC TRAP FOR A LEAD," each of which is incorporated herein in its entirety.

However, simply implementing the electrical components on the leads may not be sufficient. Leads can become faulted (e.g., breakage, shifting, insulation breaches, degradation, or other flaws that may alter electrical properties of leads), electrical components may shift or stop working overtime affecting the desired characteristics, for example. Therefore, it is important to determine, especially prior to an MRI scan, whether the leads are MRI-safe. In some situations, it may be desirable to monitor the leads and periodically check lead conditions. In accordance with techniques of this disclosure, a circuitry in the IMD may be used to monitor lead conditions and determine whether a lead is MRI-safe, in addition to detecting lead faults (e.g., shifting, breakage, or other flaws that may alter electrical properties of leads).

Signal generator 84 of IMD 16 may transmit a signal at a high frequency through the lead that is being monitored (502). Signal generator 84 may include a HF signal generator 92, which may generate signals at high frequencies, e.g., 1 Mhz or 64 MHz. Using signals with lower frequencies may allow detection of faults in a lead. However, signals with lower frequencies may yield results for MRI-safe leads that may not be clearly distinct from results associated with non-MRI-safe leads. Particularly, MRI-safe leads may be designed to have some impedance at low frequencies but go to open or short at high frequencies, depending on the type of component used (e.g., choke or trap tend to go to open impedance at higher frequencies). Therefore, for example, when a choke or trap is used to make a lead MRI-safe, higher frequencies result in making the choke or trap act like an open circuit, resulting in higher impedance, e.g., impedance goes from ~10Ω to a high impedance range ~500-3000Ω at 64 MHz. A processor (e.g., processor 80 of FIG. 3) may determine the characteristics (e.g., frequency, amplitude, timing, etc.) of the transmitted signals and store them in a memory (e.g., signal data 96).

In one example, the transmitted high frequency signal may be a burst, a pulse, or a continuous signal. In response to the transmitted high frequency signal, IMD 16 may receive a response signal (504). In some examples, the response signal may be a signal reflected in response to the transmitted signal, and may be received on the same lead on which the high frequency signal was transmitted. In other examples, the response signal may be received through another path, e.g., through another lead, or the case. In other examples, impedance of a lead may be measured while the signal is traveling in the lead. It should be noted that the signal transmission and reception may be done tip-to-ring, tip-to-case, or from any one electrode on any lead to any other electrode on another lead.

The characteristics (e.g., amplitude, frequency, timing, etc.) of the response signal may then be determined (506). The processor 80 may utilize lead analysis module 90 to analyze the received response signal (508). In analyzing the received response signal, load analysis module 90 may compare the received signal to the transmitted signal, and based on the comparison, determine the characteristics of the lead on which the high frequency signal was transmitted. For example, analysis of the signals may involve looking at the amplitude or frequency shift of the reflection response signal relative to the transmitted signal. Having knowledge of the amplitude of the transmitted signal and the amplitude of the received signal may be used to determine the amount of attenuation in the amplitude, which may be proportional to the impedance of the lead. For example, if the reflection is perfect, that may indicate an open or short at the distal end, which may be the expected behavior for some components. If, in another example, the response signal is heavily reduced in amplitude, then it may indicate attenuation along the lead, which may be expected behavior for other components. Therefore, once the received signal is analyzed, the characteristics may be compared to the expected characteristics of the lead, based on the type of component used to make the lead MRI-safe (510).

In some examples, as noted above, the comparison may be based on signal characteristics. In other examples, the impedance of the lead may be directly measured at the high frequency conditions. Impedance may be also determined proportionally by determining the lead impedance mismatch, for example. In this example, if the source has an impedance of 50Ω and the signal is nearly perfectly transmitted, then the load also had an impedance of 50Ω, whereas a load with impedance of 10Ω will transmit some of the signal and reflect most of it, and the reflected portion will be inversely proportional to lead impedance mismatch. In this example, the lead impedance mismatch may be a known characteristic for a lead that is operating properly, and a comparison between the measured mismatch and the expected mismatch may allow determination as to whether the lead is operating as expected, i.e., the lead is MRI-safe. By using a high frequency, the expected mismatch in impedance may be greater for MRI-safe leads relative to non-MRI-safe leads.

In addition to determining the impedance of the lead based on the reflected signal or during transmission of the high frequency signal through the lead, to determine whether the lead is MRI-safe, the time between the transmission of the high frequency signal and the reception of the response signal may be measured. Having knowledge of the characteristics of the lead and the signal, may allow determining the distance the signal traveled, therefore, determining the distance to the end of the lead. By comparing the calculated length of the lead with the known length of the lead, the processor may be able to determine whether there is a fault in the lead (e.g., breakage) if the calculated distance is shorter than the known length of the lead. In this manner, the same techniques used to confirm whether the lead is MRI-safe, may be also used to determine whether there is a fault in the lead. In the examples discussed in this disclosure, it should be understood that signals may be transmitted and received on leads or electrodes. For example, a signal may be transmitted and received on the same electrode, i.e., conductor coupled to the electrode, or a signal may be transmitted on one electrode and received on another electrode, where the two electrodes may be on the same lead or on two different leads.

If the processor determines that the lead is MRI-safe (512) and there are no detected faults in the lead (514), the processor may send an indication that the device is MRI-safe and to proceed with MRI scanning (516). If one of the conditions is detected as being abnormal, lead is not MRI-safe and/or the lead has faults, the processor may transmit an indication that the device/lead is not MRI-safe or is faulty (518). In some examples, the processor may determine whether the lead is MRI-safe or whether there are faults in the lead, without necessarily making a determination regarding the other condition.

The techniques of this disclosure may be performed periodically (e.g., once a day), or in response to user command (e.g., via a programmer and/or a command for an IMD to enter MRI-safe mode). In some examples, the techniques of this disclosure determine whether leads are MRI-safe and/or whether the leads have faults. The two determinations may be performed together or individually. For example, the MRI-safe determination may be performed in response to user command or upon indication of entering MRI-safe mode. In another example, lead fault detection may be performed periodically or automatically, and the periodicity of the fault detection may be set to a default value or by a user as to ensure lead integrity and functionality.

Although the disclosure is described with respect to systems that employ sensing and monitoring of cardiac activity, such techniques may be applicable to other systems in which sensing integrity is important, such as, e.g., spinal cord stimulation, deep brain stimulation, pelvic floor stimulation, gastric stimulation, occipital stimulation, functional electrical stimulation, and the like.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples of the invention have been described. These and other examples are within the scope of the following claims.

The invention claimed is:

1. A method comprising:
  transmitting, by a device, a signal through at least one medical lead implanted within at least one anatomical region of a patient,
    wherein the at least one medical lead is coupled to an electrical component configured to attenuate a predetermined frequency of energy of at least the signal, the predetermined frequency corresponding to a magnetic resonance imaging (MRI) radio-frequency (RF) energy;
  receiving, by the device, a response signal, the response signal resulting from transmission of the signal through the at least one medical lead;
  analyzing the response signal; and
  determining, based on the analysis of the response signal, whether the at least one medical lead is MRI safe and whether there is a detected fault in the at least one medical lead.

2. The method of claim 1, wherein the transmitted signal comprises a high frequency signal.

3. The method of claim 1, wherein the transmitted signal comprises a signal with a frequency selected based on the predetermined frequency of the energy attenuated by the electrical component.

4. The method of claim 1, wherein analyzing comprises:
  comparing the response signal to the transmitted signal; and
  determining an impedance mismatch associated with the at least one medical lead based on the comparison.

5. The method of claim 1, wherein analyzing comprises:
  determining a length associated with the at least one medical lead based on a time differential between the transmitted signal and the response signal; and
  comparing the determined length with an expected lead length.

6. The method of claim 1, further comprising transmitting the transmitted signal and receiving the response on an electrode of the at least one medical lead.

7. The method of claim 1, further comprising transmitting the transmitted signal on a first electrode of the at least one medical lead and receiving the response signal on a second electrode of the at least one medical lead or another medical lead.

8. The method of claim 1, further comprising transmitting an indication of the determination of whether the at least one medical lead is MRI safe and whether there is a detected fault in the at least one medical lead to an external device.

9. The method of claim 1, wherein the response signal is a signal reflected by the at least one medical lead in response to the transmitted signal.

10. The method of claim 1, wherein the response signal is a measure of an impedance in the at least one medical lead in response to the transmitted signal.

11. A medical system comprising:
  at least one medical lead configured for implantation within at least one anatomical region of a patient, wherein the at least one medical lead includes:
    at least one electrode; and
    an electrical component configured to attenuate a predetermined frequency of energy, the predetermined frequency corresponding to a magnetic resonance imaging (MRI) radio-frequency (RF) energy;
  a medical device coupled to the at least one medical lead, the medical device comprising:
    a signal generator configured to transmit a signal through the at least one medical lead;
    a sensing module configured to receive a response signal, the response signal resulting from transmission of the signal through the at least one medical lead;
    an analysis module configured to analyze the response signal; and
    at least one processor configured to determine, based on the analysis of the response signal, whether the at least one medical lead is MRI safe and whether there is a detected fault in the at least one medical lead.

12. The medical system of claim 11, wherein the transmitted signal comprises a high frequency signal.

13. The medical system of claim 11, wherein the transmitted signal comprises a signal with a frequency selected based on the predetermined frequency of the energy attenuated.

14. The medical system of claim 11, wherein:
the analysis module compares the response signal to the transmitted signal; and
the at least one processor determines an impedance mismatch associated with the at least one medical lead based on the comparison.

15. The medical system of claim 11, wherein:
the analysis module determines a length associated with the at least one medical lead based on a time differential between the transmitted signal and the response signal; and
the at least one processor compares the determined length with an expected lead length.

16. The medical system of claim 11, wherein the signal generator transmits the transmitted signal and the sensing module receives the response signal on the at least one electrode of the at least one medical lead.

17. The medical system of claim 11, wherein the at least one medical lead includes a plurality of electrodes and the signal generator transmits the transmitted signal on a first of the plurality of electrodes of the at least one medical lead and the sensing module receives the response signal on a second of the plurality of electrodes of the at least one medical lead or another medical lead.

18. The medical system of claim 11, further comprising a telemetry module configured to transmit an indication of the determination of whether the at least one medical lead is MRI safe and whether there is a detected fault in the at least one medical lead to an external device.

19. The medical system of claim 11, wherein the response signal is a signal reflected by the at least one medical lead in response to the transmitted signal.

20. The medical system of claim 11, wherein the response signal is a measure of an impedance in the at least one medical lead in response to the transmitted signal.

21. A medical system comprising:
at least one medical lead configured for implantation within at least one anatomical region of a patient, wherein the at least one medical lead includes:
at least one electrode; and
an electrical component configured to attenuate predetermined frequency of energy, the predetermined energy corresponds to an magnetic resonance imaging (MRI) radio-frequency (RF) energy;
means for transmitting, by a device, a signal through the at least one medical lead;
means for receiving, by the device, a response signal, the response signal resulting from transmission of the signal through the at least one medical lead;
means for analyzing the response signal; and
means for determining, based on the analysis of the response signal, whether the at least one medical lead is MRI safe and whether there is a detected fault in the at least one medical lead.

22. The medical system of claim 21, wherein the transmitted signal comprises a high frequency signal.

23. The medical system of claim 21, wherein the transmitted signal comprises a signal with a frequency selected based on the predetermined frequency of the energy attenuated.

24. The medical system of claim 21, wherein the means for analyzing comprises:
means for comparing the response signal to the transmitted signal; and
means for determining an impedance mismatch associated with the at least one medical lead based on the comparison.

25. The medical system of claim 21, wherein the means for analyzing comprises:
means for determining a length associated with the at least one medical lead based on a time differential between the transmitted signal and the response signal; and
means for comparing the determined length with an expected lead length.

26. The medical system of claim 21, further comprising means for transmitting the transmitted signal and receiving the response on the at least one electrode of the at least one medical lead.

27. The medical system of claim 21, wherein the at least one medical lead includes a plurality of electrodes and further comprising means for transmitting the transmitted signal on a first of the plurality of electrodes of the at least one medical lead and means for receiving the response signal on a second of the plurality of electrodes of the at least one medical lead or another medical lead.

28. The medical system of claim 21, further comprising means for transmitting an indication of the determination of whether the at least one medical lead is MRI safe and whether there is a detected fault in the at least one medical lead to an external device.

29. The medical system of claim 21, wherein the response signal is a signal reflected by the at least one medical lead in response to the transmitted signal.

30. The medical system of claim 21, wherein the response signal is a measure of an impedance in the at least one medical lead in response to the transmitted signal.

31. A non-transitory computer-readable medium comprising instructions, wherein the instructions cause a programmable processor to:
transmit, by a device, a signal through at least one medical lead implanted within at least one anatomical region of a patient,
wherein the at least one medical lead is coupled to an electrical component configured to attenuate a predetermined frequency of energy, the predetermined frequency corresponds to an magnetic resonance imaging (MRI) radio-frequency (RF) energy;
receive, by the device, a response signal, the response signal resulting from transmission of the signal through the at least one medical lead;
analyze the response signal; and
determine, based on the analysis of the response signal, whether the at least one medical lead is MRI safe and whether there is a detected fault in the at least one medical lead.

32. The non-transitory computer-readable medium of claim 31, wherein the transmitted signal comprises a high frequency signal.

33. The non-transitory computer-readable medium of claim 31, wherein the transmitted signal comprises a signal with a frequency selected based on the frequency of the energy attenuated.

34. The non-transitory computer-readable medium of claim 31, wherein the instructions to analyze comprise instructions that cause the processor to:
compare the response signal to the transmitted signal; and
determine an impedance mismatch associated with the at least one medical lead based on the comparison.

35. The non-transitory computer-readable medium of claim 31, wherein the instructions to analyze comprise instructions that cause the processor to:

determine a length associated with the at least one medical lead based on a time differential between the transmitted signal and the response signal; and compare the determined length with an expected lead length.

36. The non-transitory computer-readable medium of claim 31, further comprising instructions that cause the processor to transmit the transmitted signal and receive the response on an electrode of the at least one medical lead.

37. The non-transitory computer-readable medium of claim 31, further comprising instructions that cause the processor to transmit the transmitted signal on a first electrode of the at least one medical lead and receive the response signal on a second electrode of the at least one medical lead or another medical lead.

38. The non-transitory computer-readable medium of claim 31, further comprising instructions that cause the processor to transmit an indication of the determination of whether the at least one medical lead is MRI safe and whether there is a detected fault in the at least one medical lead to an external device.

39. The non-transitory computer-readable medium of claim 31, wherein the response signal by the at least one medical lead is a signal reflected in response to the transmitted signal.

40. The non-transitory computer-readable medium of claim 31, wherein the response signal is a measure of an impedance in the at least one medical lead in response to the transmitted signal.

* * * * *